(12) United States Patent
Ashida et al.

(10) Patent No.: US 6,450,036 B1
(45) Date of Patent: Sep. 17, 2002

(54) METHOD AND DEVICE FOR DIAGNOSING DETERIORATION OF AN ARTICLE HAVING AT LEAST A COVERING LAYER ORGANIC POLYMER MATERIAL

(75) Inventors: Tetsuya Ashida; Tsuyoshi Ikeda; Junichiro Ikehara; Masanori Fujii; Hiroshi Ishibashi, all of Hyogo; Yoshiro Habuka, Kanagawa; Minoru Okamoto, Kanagawa; Eiji Onuma, Kanagawa; Hiroshi Kato, deceased, late of Hyogo, all of (JP), Kazuko Kato legal representative (73) Assignee: Mitsubishi Cable Industries, Ltd., Amagasaki (JP)

( * ) Notice: Subject to any disclaimer, the term of this patent is extended or adjusted under 35 U.S.C. 154(b) by 0 days.

(21) Appl. No.: 09/554,787

(22) PCT Filed: Nov. 18, 1998

(86) PCT No.: PCT/JP98/05194

§ 371 (c)(1),
(2), (4) Date: Dec. 11, 2000

(87) PCT Pub. No.: WO99/27360

PCT Pub. Date: Jun. 3, 1999

(30) Foreign Application Priority Data

| Nov. 21, 1997 | (JP) | 9-320863 |
| May 26, 1998 | (JP) | 10-143852 |
| Jun. 3, 1998 | (JP) | 10-154915 |
| Jun. 3, 1998 | (JP) | 10-154929 |
| Jun. 9, 1998 | (JP) | 10-160344 |

(51) Int. Cl.$^7$ ............................................. G01N 29/04

(52) U.S. Cl. ..................... 73/584; 73/597; 73/598; 73/602

(58) Field of Search ................. 73/584, 587, 597, 73/598, 599, 600, 602, 609, 628, 799, 866

(56) References Cited

U.S. PATENT DOCUMENTS

| 4,619,143 A | * | 10/1986 | Franken ........................ 73/598 |
| 4,785,667 A | * | 11/1988 | Miyajima et al. ............. 73/618 |
| 5,456,113 A | * | 10/1995 | Kwun et al. ................... 73/587 |
| 5,457,994 A | * | 10/1995 | Kwun et al. ................... 73/587 |
| 6,076,411 A | * | 6/2000 | Horvath ........................ 73/866 |
| 6,373,245 B1 | * | 4/2002 | Kwun et al. ................. 324/240 |

FOREIGN PATENT DOCUMENTS

| JP | 63-18920 | 5/1988 |
| JP | 6-27089 | 2/1994 |
| JP | 7-35732 | 2/1995 |
| JP | 7-35733 | 2/1995 |
| JP | 9-5309 | 1/1997 |

* cited by examiner

Primary Examiner—Hezron Williams
Assistant Examiner—Jacques Saint-Surin
(74) Attorney, Agent, or Firm—Leydig, Voit & Mayer, Ltd.

(57) ABSTRACT

The invention is directed to a method and apparatus for diagnosing deterioration of an article having at least a covering layer made from an organic polymer material. The method comprises (i) forming a data group for deterioration diagnosis comprising deterioration diagnostic characteristic values and corresponding ultrasonic wave propagation characteristic values for samples having different material specifications, (ii) propagating an ultrasonic wave through the covering layer of the article to measure an ultrasonic wave propagation characteristic of the covering layer, and (iii) determining a corresponding deterioration diagnostic characteristic from the data group for the ultrasonic wave propagation characteristic of the covering layer. The apparatus comprises (i) an ultrasonic wave propagation measuring device comprising an ultrasonic wave transmitting means, an ultrasonic wave receiving means, a delay chip, and a propagation time measuring means, (ii) a storage unit containing a data group for deterioration diagnosis, and (iii) a central processing unit.

15 Claims, 7 Drawing Sheets

S1: input of kind of material
S3: input of kind of plasticizer
S5: input of amount of filler
S6: amounts of plasticizer and filler
S7: input of amounts of filler and carbon
S8: input of amounts of filler and carbon

METHOD AND DEVICE FOR DIAGNOSING DETERIORATION OF AN ARTICLE HAVING AT LEAST A COVERING LAYER ORGANIC POLYMER MATERIAL

TECHNICAL FIELD

The present invention relates to a method for diagnosing deterioration of an article (typically a cable) having at least a covering layer made from an organic polymer material and an apparatus therefor.

BACKGROUND ART

A covering layer (insulating layer made from an organic polymer material) of an installed cable changes with the time elapsed due to various factors and shows degraded electric insulating property. To prevent this, a periodic inspection is necessary to diagnose deterioration level. For this purpose, various deterioration diagnostic methods have been proposed.

Of the proposed methods, the method for diagnosis of deterioration by propagating an ultrasonic wave (JP-A-7-35732, JP-A-7-35733) is superior in that it does not require destruction of the cable. The method described in these publications includes propagating an ultrasonic wave through the covering layer of the installed cable, based on which an ultrasonic wave propagation velocity is calculated, and converting the velocity to physical property such as breaking elongation percentage and hardness of the covering layer. The level of deterioration is diagnosed based on the obtained property.

The measurement method of the propagation velocity in the above-mentioned publications using an ultrasonic wave is outlined in the following. An ultrasonic wave enters from the surface of the covering layer of the cable toward the center of the cable, and the time t is measured, which is necessary for the ultrasonic wave to reflect from the interface between the covering layer and the layer beneath (e.g., conductor) and to return to the position of incidence. Using this t and the thickness a of the covering layer, V=2a/t is calculated. This V is taken as the propagation velocity of ultrasonic wave in the covering layer.

The measurement method of the above-mentioned publications is problematic in that it uses thickness a of the covering layer for the calculation of propagation velocity V of the ultrasonic wave. Namely, when the thickness a of the covering layer can be known with high precision, the above-mentioned measurement method is useful, but the value a cannot be known accurately with regard to an actually installed article, such as a cable, which does not permit breakage. By referring to a design specification, for example, the standard size a as designed can be known, but the actual size of a may be considerably different because a production tolerance of ±15% of the standard size on design is allowed for the production of an insulating electric wire. Therefore, the propagation velocity calculated using the value a obtained in a non-destructive manner and the deterioration diagnosis based thereon show low precision.

It is therefore an object of the present invention to provide a more preferable deterioration diagnostic method for diagnosing deterioration level of an article (e.g., cable) having at least a covering layer made from an organic polymer material, by the use of an ultrasonic wave, as well as a deterioration diagnostic apparatus preferable for practicing the method.

DISCLOSURE OF THE INVENTION

The deterioration diagnostic method of the present invention is a method for diagnosing deterioration of an article having at least a covering layer made from an organic polymer material. The method is characterized in that the deterioration diagnostic characteristic and the corresponding ultrasonic wave propagation characteristic of a covering layer sample are measured, a data group for the deterioration diagnosis is formed, wherein the value of deterioration diagnostic characteristic and the value of ultrasonic wave propagation characteristic correspond to each other, an ultrasonic wave is propagated through the surface and near surface of the covering layer of an article to measure the ultrasonic wave propagation characteristic of the covering layer, and the deterioration diagnostic characteristic corresponding to the ultrasonic wave propagation characteristic is obtained from the aforementioned data group.

The deterioration diagnostic method of the present invention comprises the steps of changing, when preparing the data group for the deterioration diagnosis, the material specification consisting of one or more factors selected from the group consisting of the kind of the organic polymer material, the kind of plasticizer contained in this organic polymer material, the amount of plasticizer added, the amount of filler added, and the amount of carbon added, and measuring deterioration diagnostic characteristic and ultrasonic wave propagation characteristic corresponding thereto of samples having different material specifications to form a data group for deterioration diagnosis, measuring the ultrasonic wave propagation characteristic of the covering layer of an article, and obtaining the deterioration diagnostic characteristic corresponding to the aforementioned ultrasonic wave propagation characteristic from the data group having the material specification equivalent to this covering layer.

In the deterioration diagnostic method of the present invention, the above-mentioned ultrasonic wave propagation characteristic is the propagation velocity of an ultrasonic wave, which is measured by setting an ultrasonic wave transmitting means and an ultrasonic wave receiving means on the surface of a measurement target respectively via a delay chip, thereby to make an ultrasonic wave sent from the aforementioned transmitting means linearly propagated in the measurement target to the position of the aforementioned receiving means and received by the receiving means, measuring propagation times t1 and t2 of the ultrasonic wave when the intervals between the aforementioned transmitting means and the aforementioned receiving means are L1 and L2, respectively, and calculating (L2−L1)/(t2−t1) to give the propagation velocity of the ultrasonic wave.

In the deterioration diagnostic method of the present invention, the above-mentioned ultrasonic wave propagation characteristic is the propagation time of an ultrasonic wave that has been transmitted a certain distance. The covering layer of a specimen or article is the test target, and an ultrasonic wave transmitting means and an ultrasonic wave receiving means are each set on the surface of the test target via a delay chip at the aforementioned certain distance. Then, the time necessary for the ultrasonic wave sent from the aforementioned transmitting means to be linearly transmitted through the test target to the position of the aforementioned receiving means and to be received by the receiving means via the delay chip is measured.

The deterioration diagnostic method of the present invention measures the distribution of the deteriorating factors that cause deterioration of the covering layer of the above-mentioned article, which is an installed cable, in the longitudinal direction of the cable and make a diagnosis of the portion showing greater levels of deteriorating factors.

According to the deterioration diagnostic method of the present invention, the above-mentioned deterioration diagnostic characteristic value of the covering layer of an article is taken as E1; a heating temperature t and the corresponding heating time h at various deterioration diagnostic characteristic values are measured after changing the deterioration diagnostic characteristic values, inclusive of limit of use value Ez, for a specimen made of the same material as the covering layer, thereby to give a data group used for remaining life prediction; using this data group for remaining life prediction, wherein the period of use of the aforementioned article is regarded as a heating time h1, the heating temperature t1 corresponding to the heating time h1 at the deterioration diagnostic characteristic value of E1 is determined; the heating time hz corresponding to the heating temperature t1 at the limit of use value Ez of the deterioration diagnostic characteristic is determined; and the value of hz–h1 is taken as the remaining life.

The deterioration diagnostic apparatus of the present invention is an apparatus for diagnosing the deterioration of an article having at least a covering layer made from an organic polymer material and comprises at least the measuring device of the following (A):

(A) a measuring device for ultrasonic wave propagation characteristic wherein a covering layer of an article or a specimen of a covering layer is a measurement target, comprising an ultrasonic wave transmitting means, an ultrasonic wave receiving means, a delay chip of the following (A1) to be intervened when these means are set on the surface of the measurement target, and a propagation time measuring means to measure the time spent from transmission of an ultrasonic wave from the aforementioned transmitting means to its receipt by the receiving means:

(A1) a delay chip whose inclination and material have been determined such that the propagating direction of the ultrasonic wave changes when it enters the measurement target from the delay chip, as a result of which the ultrasonic wave is propagated through the surface and near surface of the measurement target.

DETAILED DESCRIPTION OF THE INVENTION

The deterioration diagnostic method of the present invention comprises at least the following steps.

(1) Preparation of a specimen made from the same material as the covering layer of a diagnosis target article (e.g., installed cable), measuring deterioration diagnostic characteristic (hereinafter diagnostic characteristic) and the corresponding ultrasonic wave propagation characteristic (hereinafter propagation characteristic) of the specimen, and preparation of a data group for the deterioration diagnosis wherein a diagnostic characteristic value corresponds to a propagation characteristic value.

(2) Propagating an ultrasonic wave in the diagnosis target article through the surface and near surface of the covering layer to measure the propagation characteristic of the covering layer.

(3) Determining, using the data group of the above-mentioned (2), diagnostic characteristic corresponding to the propagation characteristic of the article as obtained by the measurement of the above-mentioned (1), and diagnosing the article for deterioration based on the diagnostic characteristic.

The article to be the deterioration diagnosis target only need to have at least a covering layer made from an organic polymer material, and is exemplified by cable, pipe, hose, sheet, surface material (e.g., wall material and floor material) and the like. The cable encompasses any electric wire having a covering layer made from an organic polymer material. Examples thereof include insulating electric wire, power cable etc. irrespective of use such as communication, electric power, equipment etc. For these cables, deterioration of the covering layer is an important problem. Since installed cables cannot afford destructive inspection, the utility of the present invention becomes most significant when such cable is the target of the deterioration diagnosis.

The diagnostic characteristic shows deterioration level of an organic polymer material used for a covering layer (hereinafter also referred to as covering layer material) and need only have a correlation with propagation characteristic. For example, the diagnostic characteristic may be mechanical properties and electrical properties such as surface rebound hardness of material, surface needle puncture hardness, tensile strength, breaking elongation percentage, elastic modulus, Young's modulus, modulus, dielectric constant, dielectric dissipation factor, volume resistivity, alternating current breakdown voltage strength, impulse breakdown voltage strength, torsion torque and flexural rigidity when an article is long (e.g., cable), and the like. Particularly, the breaking elongation percentage clearly shows the degree of deterioration of the covering layer of a cable, and also a strong correlation with propagation characteristic. As such, it is preferably used as diagnostic characteristic.

When the breaking elongation percentage of the covering layer of a cable approaches 50%, cracks tend to occur due to vibration and impact. When water invades from the outside, therefore, a dielectric breakdown may occur. A cable may be exchanged when the breaking elongation percentage reaches approximately 50%. However, the index of deterioration may be standardized appropriately by the user.

The propagation characteristic is an amount showing the propagation state when an ultrasonic wave is propagated through the material of a covering layer, and need only have a correlation with the deterioration of a material. For example, it may be a propagation time when the propagated distance is constant, a propagation velocity calculated from propagated distance and propagation time, sensitivity of ultrasonic wave reception, frequency change of ultrasonic waveshape, change of ultrasonic waveshape, damping characteristic of ultrasonic wave and the like. Particularly, propagation time and propagation velocity are useful. The measurement method of the propagation characteristic is to be explained later when the apparatus is explained.

The organic polymer material to be used for the covering layer is exemplified by the following.

A thermoplastic resin includes polyolefin type such as polyethylene, polypropylene, polybutene, poly-4-methylpentene-1, ethylene-vinylacetate copolymer, ethylene-ethylacrylate copolymer and the like, polyamide such as nylon, polyvinyl chloride, polyvinylidene chloride, thermoplastic polyester and the like.

The rubber may be natural rubber, isoprene rubber, butyl rubber, ethylene-propylene copolymeric rubber, ethylene-propylene-diene ternary copolymeric rubber, styrene-butadiene copolymeric rubber, acrylonitrile-butadiene copolymeric rubber, ethylene-vinylacetate copolymeric rubber, ethylene-ethylacrylate copolymeric rubber, chlorosulfonated polyethylene rubber, epichlorohydrin rubber, silicone rubber, fluororubber and the like.

The thermoplastic elastomer may be a styrene type thermoplastic elastomer such as ABA type triblock, $(AB)_nX$ type radial block etc., a polyolefin type thermoplastic elastomer such as blended TPO, partially crosslinked blended TPO, completely crosslinked blended TPO etc., a polyvinyl chloride type thermoplastic elastomer such as nitrile rubber blend, partially crosslinked nitrile rubber blend etc., a polyurethane type thermoplastic elastomer such as polyester type, polyether type etc., a polyester type thermoplastic elastomer such as polyester-polyether type, polyester-polyester type etc., and the like.

The data group may be continuous or discontinuous. That is, it may consist of a record of diagnostic characteristic that changes continuously and the propagation characteristic that responsively changes continuously, or it may consist of a record of varying diagnostic characteristic values obtained at specific intervals and propagation characteristic values corresponding thereto. The data group is preferably prepared with regard to various materials in advance of diagnosis of an article. If such data are always retained for review at any time, diagnosis results are quickly obtained from the measurement of an article using an ultrasonic wave.

When the data group is prepared, the "diagnostic characteristic" and the "propagation characteristic" may constitute a binary correspondence data group. Alternatively, a factor of "time elapsed" may be added to form a tertiary correspondence data group including "time elapsed", "diagnostic characteristic" and "propagation characteristic". Further factors may be added to constitute a multilateral correspondence data group. As mentioned later, a special data group may be formed for the prediction of remaining life, wherein "specific deteriorating factor value", "time elapsed" and "diagnostic characteristic" correspond to each other.

By adding "time elapsed" as a factor to the data group, the data group no longer merely teaches the level of the values of mechanical property and electrical property of a material. It also teaches changes with the course of time of the diagnostic characteristic from the change with the course of time of the propagation characteristic, and from the change, the degree of deterioration of an article can be diagnosed. In addition, a total diagnosis including evaluation relating to the time elapsed becomes available, such as evaluation of an article in terms of deterioration for the time used, prediction of remaining life (residual life) and the like. Particularly, prediction of remaining life makes a diagnosis of, not the deterioration up to the time point of measurement, but the progress of deterioration after the time point of measurement, which is a useful deterioration diagnosis of facilities such as cable and the like.

A data group can be formed by deteriorating a sample by changing the conditions of radiation, heating and the like, measuring the varied diagnostic characteristic, simultaneously measuring the propagation characteristic at that time, and recording the one-to-one measures. When a sample is to be deteriorated and when the article is a cable, it can be deteriorated according to the environment in which the cable is installed. For example, a cable installed in a facility in an atomic power plant can be deteriorated with a radiation dose of not more than 10 kGy/h at a temperature of 250° C. or less. A sample may be deteriorated at a higher speed under severer conditions, such as in an acceleration test, but when the factor of "time elapsed" is added to the data group in an acceleration test, the accelerated time elapsed and the time elapsed under actual use environment preferably correspond to each other to allow conversion.

When the target of the deterioration diagnosis is a cable and the material of a covering layer is polyvinyl chloride, a phthalate ester type or trimellitate ester type plasticizer, and a filler are generally added. When the material is a rubber type material or a polyethylene type material, a filler and carbon are generally added.

In the present invention, it should be noted that variation in the kind and amount of plasticizer, filler and the like to be added to the material of a covering layer results in a different correlation between propagation characteristic and diagnostic characteristic. Therefore, one or more members from the kind of plasticizer, the amount of plasticizer, the amount of filler and the amount of carbon is/are changed per one kind of the material of a covering layer to determine material specifications, and samples having different material specifications are measured for diagnostic characteristic and the corresponding propagation characteristic, with which a data group is preferably formed.

The article to be the target of diagnosis is determined for propagation characteristic and for the above-mentioned material specification. The combination of the propagation characteristic and material specification is converted to the diagnostic characteristic against the above-mentioned data group, and a deterioration diagnosis is made according to the material specification.

For example, a cable is subjected to the following steps (1) to (3) for diagnosis.

(1) Determining the relationship between propagation characteristic and diagnostic characteristic (physical property and/or electrical property) of each organic polymer material when the kind of plasticizer, the amount of plasticizer, the amount of filler and the amount of carbon to be added according to each organic polymer material of a covering layer of a cable are changed as parameters, thereby to form a data group.

(2) Selecting at least one relationship between propagation characteristic and diagnostic characteristic from the data group of the above-mentioned (1), based on the information obtained from the covering layer of the cable to be the diagnosis target.

(3) Determining the propagation characteristic of the covering layer of the diagnosis target cable, and after combining with the relationship selected in (2), determining the diagnostic characteristic of the covering material of the cable, based on which the deterioration level of the covering layer of the cable is diagnosed.

According to the experiment done by the present inventors, when the material of the covering layer is polyvinyl chloride, the amount of phthalate ester type plasticizer does not affect the correlation between the propagation characteristic and the diagnostic characteristic, but the amount of trimellitate ester type plasticizer does. As to the filler, its amount affects the correlation but its kind does not. When the material is chloroprene rubber (without filler), the amount of carbon affects the correlation. When the material is polyethylene, the amount of filler affects the correlation.

The information of the covering material of the cable (diagnosis target), such as the kind of polymer material, the kind of plasticizer, the amount of plasticizer, the amount of filler and the amount of carbon, which are contained in the polymer material, can be obtained as follows.

The kind of polymer material can be determined non-destructively from hardness of the cable covering material, installation record and production record. Generally, the only judgement is if it is polyvinyl chloride, a rubber type material or a polyethylene type material. If the cable has something printed on, its kind will be known. For example, "IV" printed on the surface of the cable means a vinyl insulating cable and "CV" means a crosslinked polyethylene insulating vinyl sheath. When it cannot be determined in the above manner, a small amount of the cable covering material is sampled and subjected to thermogravimetric analysis or infrared absorption spectrum measurement.

The kind and the amount of a plasticizer can be known from installation record and production record. When they cannot be determined in this manner, for example, the surface of the covering material of the installed cable is rubbed with absorbent cotton containing a solvent (e.g., acetone, methanol, THF etc.) to collect plasticizer. The component in the absorbent cotton can be determined non-destructively by the analysis using infrared absorption spectrum, GPC (Gel Permeation Chromatography) or HPLC (High Performance Liquid Chromatography).

The amount of a filler can be known from installation record and production record. If this method is not successful, a small amount of a sample (a few milligrams) is taken from the installed cable and subjected to the analysis by TGA (thermogravimetric analysis). The amount of carbon can be known in the same manner.

As explained earlier, the kind of plasticizer is determined as necessary when the polymer material is polyvinyl chloride. In general, the plasticizer used is a phthalate ester plasticizer. When heat resistance is required, a trimellitate ester type plasticizer is used. The amount of plasticizer is determined as necessary when the plasticizer is of a trimellitic acid type. The amount of carbon is determined as necessary when the polymer material is a rubber type material or a polyethylene type material.

In the present invention, an ultrasonic wave is propagated through the surface and near surface of the covering layer of an article to measure propagation characteristic. The method for measuring the propagation characteristic is explained in the following while referring to a part of the deterioration diagnostic apparatus of the present invention.

Figure 1:
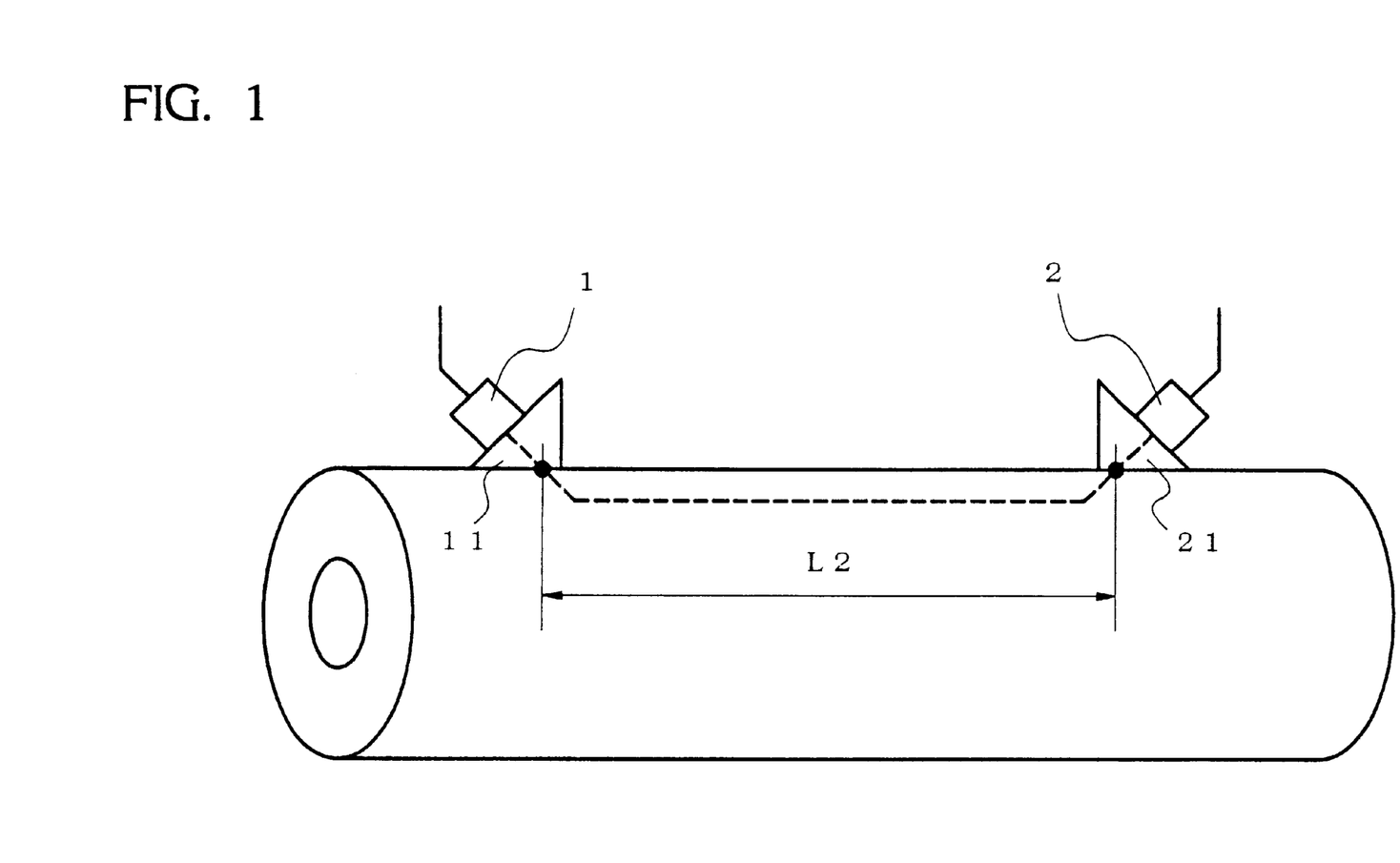
FIG. 1 shows one embodiment of the deterioration diagnostic apparatus of the present invention, which is under deterioration diagnosis of a cable, wherein a driving system and the like are omitted.

The deterioration diagnostic apparatus of the present invention contains at least a measuring device (A) shown in FIG. 1. This measuring device (A) comprises an ultrasonic wave transmitting means (hereinafter transmitting means) 1, an ultrasonic wave receiving means (hereinafter receiving means) 2, delay chips 11, 21 installed respectively for these means, and a propagation time measuring means 3.

The propagation time measuring means 3 measures the time (propagation time) from the transmission of an ultrasonic wave by the aforementioned transmitting means to its receipt by a receiving means.

The delay chips 11, 21, to be explained in detail later, are interposed between the transmitting means 1 or the receiving means 2 and the surface of the measurement target. They refract an ultrasonic wave toward the direction along the surface of the measurement target or receive the ultrasonic wave transmitted along the surface.

The transmitting means 1 contains at least an ultrasonic wave piezoelectric transducer (not shown) within inside. The ultrasonic wave piezoelectric transducer is a transducing element that converts an electric signal to an ultrasonic wave. The transmitting means 1 can transmit the ultrasonic wave sent from the piezoelectric transducer to the inside of the covering layer of the measurement target. The transmitting means 1 is set on the surface of the covering layer C1 of cable C (one example of measurement target) via a delay chip 11.

The receiving means 2 contains at least an ultrasonic wave detecting element (not shown) within inside. The ultrasonic wave detecting element is a transducing element that converts an ultrasonic wave to an electric signal. The receiving means 2 can convert the ultrasonic wave sent from the transmitting means and propagated through the covering layer into an electric signal by the action of the detecting element and receives the signal. The receiving means 2 is set on the surface of the covering layer C1 of cable C via a delay chip 21 at a distance L1 from the transmitting means 1.

According to the structure of the above-mentioned measuring device (A), the ultrasonic wave sent from the transmitting means 1 enters the measurement target covering layer via the delay chip 11. The delay chip 11 is made from a material selected to achieve ultrasonic wave propagation velocity and in view of the material of the covering layer, and has a selected inclination. Therefore, as explained by the Snell's law, the ultrasonic wave changes its course of propagation at the interface between the delay chip and the covering layer, is linearly propagated through the surface and near surface of the covering layer to the position of the receiving means, and received by the receiving means 2 via the delay chip 21. The propagation time t at that time is measured by a propagation time measuring means 3.

The ultrasonic wave is propagated through the surface and near surface of the covering layer alone (hereinafter to be expressed as "along the surface of covering layer") and directly communicated between the transmitting means and the receiving means. Consequently, the propagation characteristic can be determined only from the amount measured from the outside, wherein difficult measurements of, for example, the thickness of the covering layer, are unnecessary. The deterioration diagnostic apparatus of the present invention containing the above-mentioned measuring device (A) enables preferable application of the deterioration diagnostic method of the present invention.

Figure 2:
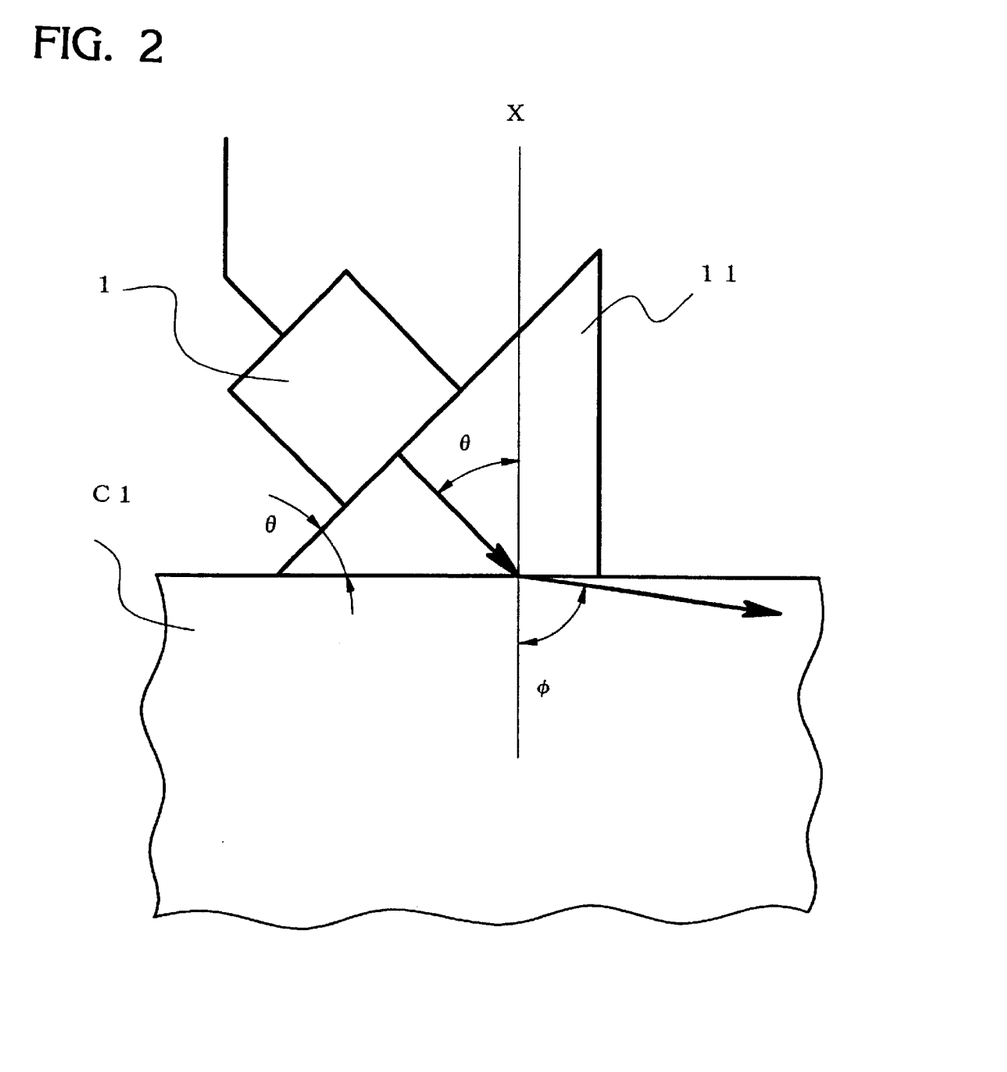
FIG. 2 explains the construction of a delay chip.

A delay chip is explained by referring to the transmission side as an example. As shown in FIG. 2, the delay chip has a cotter-like slant to mount an ultrasonic wave piezoelectric transducer (detecting element in the receiving means), and is interposed between the vibration plane of the ultrasonic wave piezoelectric transducer and the surface of the measurement target to form an angle θ. This angle θ becomes an angle of incidence θ (angle formed with normal X of surface). The basic structure of the delay chip is shown in the prior art. In FIG. 2, the transmitting means 1 is set on the surface of the covering layer C1 of the measurement target C via the delay chip 11. In FIG. 2, the material of the delay chip has been determined to meet [propagation velocity V1 of ultrasonic wave in delay chip]<[propagation velocity V2 of ultrasonic wave in the material of covering layer].

By the action of delay chip 11, the ultrasonic wave enters the covering layer C1 at an incidence of θ, is refracted at the interface to form a refractive angle φ and propagates through the covering layer C1. This is as explained by the Snell's law (law of refraction).

In the present invention, V1 relative to V2 and θ are determined such that the ultrasonic wave after refraction propagates along the surface of the covering layer. In effect, it is possible to obtain a component that propagates along the surface of the covering layer even if slightly deviated from the Snell's law, but it is more efficient to follow the Snell's law.

In the present invention, an ultrasonic wave is propagated through the surface and near surface of the covering layer. The surface and near surface of the covering layer through which the ultrasonic wave is propagated is mainly the area covering about 3 mm depth from the surface of the covering layer. Therefore, when the covering layer is sufficiently thick, no problem is caused, but when the thickness is, for example, only 1.5 mm, a part of the ultrasonic wave is reflected from the interface with a lower layer of the covering layer (conductor in the case of cable and the like, a layer next to and beneath the covering layer), or repeats reflection between the interface and the surface of the covering layer. The propagation in this way may not permit accurate measurement of propagation characteristic. For accurate measurement, therefore, an ultrasonic wave is preferably propagated through the surface of the covering layer or to about 1 mm deep from the surface, thereby preventing the wave from reaching the lower layer, linearly from the transmitting means to the receiving means.

The material of the delay chip is determined in view of the material of the covering layer, so that V1 is not more than 1.1 times the value of V2, more preferably not more than V2, particularly preferably not more than 0.97 time the value of V2. When V1<V2, then incidence θ<refractive angle φ, which is in conformity with the Snell's law and more efficient. In this case, θ is preferably about 20°–85°.

An undeteriorated organic polymer material has a propagation velocity V1 of about 1800 m/s for polyethylene, about 1800 m/s for polyvinyl chloride, about 1350 m/s for ethylene-propylene copolymeric rubber (EPM), about 1300 m/s for polyethylene tetrafluoride, about 1000 m/s for silicone rubber, and the like. Therefore, when the measurement target is polyethylene, polyvinyl chloride or ethylene-propylene copolymeric rubber (EPM), the material of the delay chip is preferably polyethylene tetrafluoride or silicone rubber because V1<V2 is satisfied.

The ultrasonic wave to be used in the present invention is not limited with regard to frequency. An organic polymer material, such as polyethylene, polyvinyl chloride, ethylenepropylene copolymeric rubber (EPM) and the like, which is often used for the covering layer of a cable generally shows greater damping of ultrasonic wave. Thus, a frequency of about 0.1–5 MHz, particularly about 0.5–2 MHz, associated with relatively less damping, is preferable.

The construction of the apparatus as a whole including other factors of the deterioration diagnostic apparatus of the present invention is explained after referring to the deterioration diagnostic method.

In the present invention, two methods of (I), (II) are preferably provided as the measurement method of propagation characteristic. Either method is preferably applied with the deterioration diagnostic apparatus of the present invention. These methods are described in the following.

The method (I) uses propagation velocity as the propagation characteristic, and therefore, measures the propagation velocity. As shown in FIG. 1, it includes transmitting means 1 and receiving means 2 set on the surface of the measurement target via delay chips 11, 21, respectively. As is clear from the explanation of the apparatus, the ultrasonic wave sent from the transmitting means 1 is linearly propagated along the surface of the measurement target to the position set of the receiving means 2. The interval between the transmitting means 1 and the receiving means 2 is set to L1 or L2, and each total propagation time t1 or t2 is measured.

The following formulas (1), (2) are satisfied when propagation velocity is V11, propagated distance is L11 and propagation time is t11 in the delay chip 11; propagation velocity is V21, propagated distance is L21 and propagation time is t2 in the delay chip 21; and propagation velocity is V, propagation time is tx when interval set (=propagated distance) is L1, and propagation time is ty when propagated distance is L2 in the covering layer C1:

$$t1 = t11 + tx + t21 = (L11/V11) + (L1/V) + (L21/V21) \quad (1)$$

$$t2 = t11 + ty + t21 = (L11/V11) + (L2/V) + (L21/V21) \quad (2)$$

From the above formulas (1)–(2), the propagation velocity $V=(L2-L1)/(t2-t1)$ can be obtained. As is clear from this formula, the propagation velocity V in the covering layer C1 can be obtained only from the interval set and the total propagation time, irrespective of the propagation time consumed by the delay chip, the thickness of the covering layer and the like.

The deterioration diagnostic apparatus of the present invention preferably contains an interval measuring means to measure the distance between the transmitting means 1 and the receiving means 2. This measuring means may have not only a mere measuring function but also a function to set the interval between the transmitting means and the receiving means to a desired value. For example, a structure that directly reads and fine-tunes the interval between the transmitting means and the receiving means by utilizing a micrometer head and the like can be equipped.

The ultrasonic wave that transmits through a solid, particularly an organic polymer material, is extremely susceptible to damping. Therefore, L1 and L2 are preferably set to a value from about several hundred micrometers to several dozen millimeters.

The method (II) uses the total propagation time from oscillation to detection while setting the propagated distance as the propagation characteristic constant. A method for the measurement of a propagation time is the same as in the above-mentioned method (I) for the total propagation times t1 and t2. The use of the deterioration diagnostic apparatus of the present invention is preferable.

In this method (II), the propagation time is measured constantly at the same propagated distance in the measurement for preparation of a data group or measurement of an article. Preferably, measuring apparatuses having the same specification are used. When the delay chip is always set to have the same specification and the interval set is always set to be constant, the amount subject to change is substantially the propagation velocity alone which varies according to the deterioration of the covering layer, whereby the propagation time and the diagnostic characteristic are made to directly correspond to each other. Inasmuch as the propagation time is always used for the evaluation, calculation and the like necessary for erasing the time relating to the delay chips included in the above-mentioned method (I) are obliterated. That is, the propagation time of the covering layer of an installed cable is measured only once, and the obtained measure corresponds to the diagnostic characteristic in the data group. As a result, the deterioration diagnosis becomes easy and accurate. Combined with the above-mentioned factor of "time elapsed", an accurate overall diagnosis inclusive of change with time and the like is facilitated by a simple measurement of the propagation time of an article.

The present invention takes note of the fact that, when an article is long, the degree of deterioration varies along the longitudinal direction thereof. This is explained with regard to a cable. An installed cable is exposed to an environment that varies markedly in the longitudinal direction of the cable, and the deterioration level of the covering layer also varies drastically in the longitudinal direction to the degree worth while taking note of. In a conventional deterioration diagnostic method, since this aspect is ignored in the selection of the part to be diagnosed, the diagnosis results and actual level of deterioration could be strikingly different.

In the present invention, the distribution of the deteriorating factor that deteriorates the covering layer of the cable along the longitudinal direction thereof is measured, based on which the part where a deteriorating factor exerts a great influence is subjected to the deterioration diagnosis. In this way, the diagnosis reflects the actual deterioration state. By knowing the part where a deteriorating factor influences greatly and improving the environment where the part is in, the progress of the deterioration of the cable can be deferred and its service life can be prolonged.

The method for determining the distribution of deteriorating factors in the longitudinal direction of the installed cable is not limited. For example, using one means for measuring the deteriorating factor, an installed cable may be examined along the longitudinal direction. Alternatively, measuring means (devices) may be set along the longitudinal direction of an installed cable at least over a certain part thereof, and simultaneous measurements at multiple sites may be done.

The deteriorating factor includes those causing chemical deterioration of the material of a covering layer, such as temperature, humidity and water, pH of a substance surrounding the covering layer, oil, hydrogen sulfide, oxygen, ozone, other reactive gases, sunlight, radiation and the like; and those causing mechanical deterioration of the material of a covering layer, such as various forces acting from the inside or outside of the cable, and vibration, strain and the like generated in any part of a cable. Important deteriorating factors are to be selected from those and the distribution of the selected factors is determined using a measuring apparatus capable of detecting the factors.

The measurement interval or the interval set between the measuring apparatuses along the cable can be determined in consideration of the state of installation and environment of the cable. For example, outdoor radiation dose, concentration of reactive gas in the air such as hydrogen sulfide, oxygen, ozone and the like, humidity, amount of light and the like are almost the same over a relatively wide area. Therefore, an interval of about 5–50 m is sufficient. In contrast, exposure of a covered cable wired in an atomic power plant to the radiation dose, immersion in water, adhesion of oil etc. to the covered cable on-street installed in a production plant occur in a relatively small area. Therefore, an interval of about 1–10 m, sometimes about 0.5–2 m, is preferable.

The following explains the case wherein an apparatus for the measurement of deteriorating factor is set along the cable. For example, when the temperature is to be measured, the thermosensitive part of the measuring apparatus is set to come into contact with the surface of the covered cable using, for example, an adhesive tape. When the air humidity, a substance surrounding a cable, hydrogen sulfide concentration, oxygen concentration, amount of sunlight or radiation dose is to be measured, a sensing part of the measuring apparatus is set in adjacency to or near the covered cable, for example, at about 1–50 cm from the surface of the covered cable. The presence of oil adhered to the surface of the covering layer of a cable can be detected by using a sensor containing rubber in a sensing part, which swells with oil and shows different electric resistance. When the force acting on the cable or a strain generated on the cable is to be detected, a strain gauge is set on the surface of the covering layer.

The deteriorating factors are measured continuously or at certain time intervals. The time interval varies depending on the deteriorating factor and the article (particularly cable). For example, about once an hour, once a day, or once a year may be sufficient.

As stated earlier, one of the deterioration diagnoses of the present invention is prediction of the remaining life. That is, a diagnosis of the degree of deterioration expressed by the remaining time up to the limit of use. In the present invention, by adding "time elapsed" as a factor to the data group, a preferable prediction method of the remaining life is provided. The method is explained next by referring to a cable as an example of the article.

According to the present invention, the remaining life is predicted according to the following steps.

(1) Measuring, according to the deterioration diagnostic method of the present invention, the ultrasonic wave propagation characteristic of the covering layer of an installed cable, and obtaining the corresponding diagnostic characteristic value E1 from the data group for deterioration diagnosis.

(2) Forming a data group for remaining life prediction with regard to a specimen made from the same material as the covering layer. The data group for remaining life prediction contains diagnostic characteristic value E, heating temperature w and heating time h corresponding to each other. The correspondence of the (diagnostic characteristic value E, heating temperature w, heating time h) will be explained in detail later. The diagnostic characteristic value E includes a value Ez determined to show the limit of use.

(3) Predicting the remaining life as follows from E1 measured above and the data group for remaining life prediction.

(a) The period of use of the installed cable is considered to be a heating time h1.

(b) The heating temperature w1 corresponding to the heating time h1 when diagnostic characteristic value is E1 is determined from the data group for remaining life prediction.

(c) The heating time hz corresponding to the heating temperature w1 when diagnostic characteristic value is Ez is determined from the data group for remaining life prediction.

(d) The difference between hz and h1 (hz−h1) is taken as the remaining life.

The above-mentioned steps (1)–(3) are explained in more detail using actual data, wherein the article is a cable and the diagnostic characteristic is a breaking elongation percentage.

For the step (1), the deterioration diagnostic method of the present invention can be used, which is as explained above.

Figure 5:
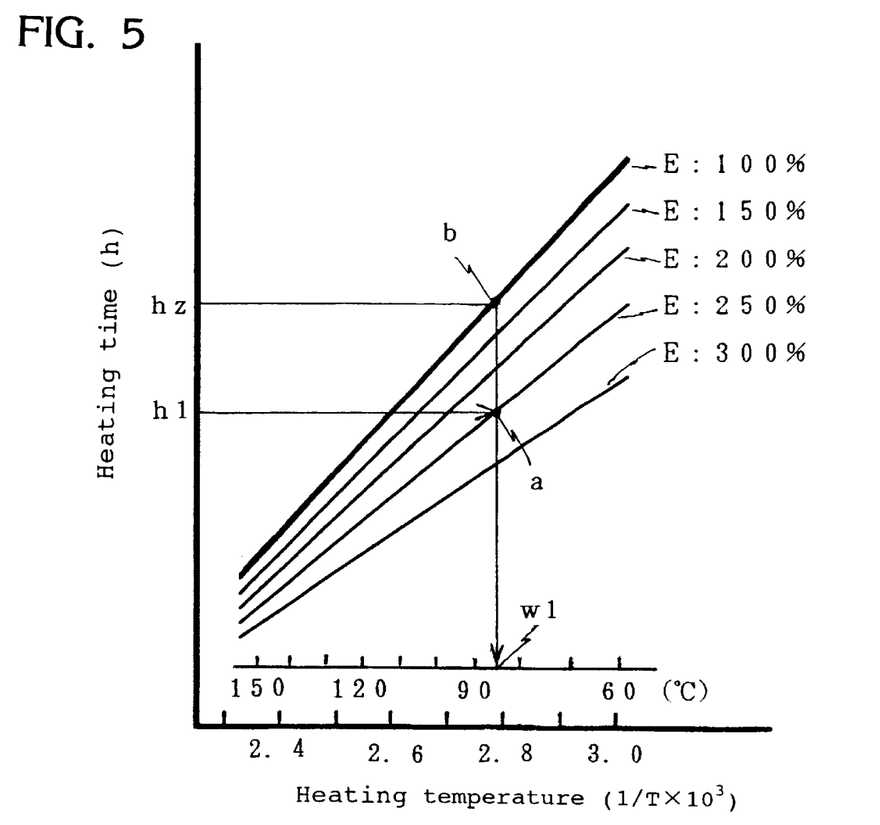
FIG. 5 is a graph showing the relationship between heating temperature (axis of abscissa) and heating time (axis of ordinate) at each breaking elongation percentage, wherein the axis of abscissa is a reciprocal of absolute temperature T as a heating temperature and the axis of ordinate is a logarithm of heating time h.

The step for forming the data group for remaining life prediction in step (2) is exemplarily shown. The data group for remaining life prediction in this step contains, as shown in FIG. 5, diagnostic characteristic value E, heating temperature w and heating time h, that correspond to each other. To be specific, the data group shows a correlation between w and h (hereinafter w–h correlation) at each value of E wherein E varies as a parameter.

The material of the specimen to be used for tentatively establishing the w–h correlation may be a material having the same composition as the material of the covering layer of the cable to be the target of the remaining life prediction, or may be a similar material. The similar material can be any as long as it is based on the original organic polymer material and has a deterioration diagnostic characteristic E within ±20% deviation. A sheet (e.g., thickness about 1–5 mm) specimen is obtained by press processing. The specimen may be an undeteriorated target itself of the remaining life prediction, instead of the aforementioned sheet.

Figure 4:
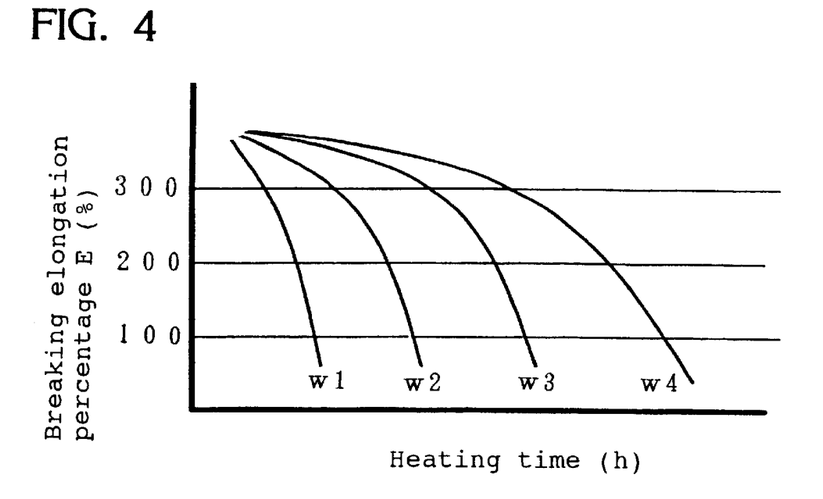
FIG. 4 is a graph showing the relationship between heating time h (axis of abscissa) and breaking elongation percentage E (axis of ordinate) at each heating temperature w.

The preferable step for forming the data are as follows. A specimen is heated at various heating temperatures w. variation in breaking elongation percentage E relative to heating time h is measured at each heating temperature w, a relationship curve between h and E at each value of w is drawn, as shown in FIG. 4, which is converted to the relationship curve between h and w at each value of E, as shown in FIG. 5, and preferably used as the data group for remaining life prediction. The value E includes value Ez determined as the limit of use. Ez can be set in consideration of the kind of material, management standard for user and other factors.

The heating temperature w preferably covers a wide temperature range and is marked at small distances. Generally, heating at a low temperature of not more than 90° C. causes slow progress of deterioration. Therefore, at least 50° C., particularly 20° C., marking over the range of 100–200° C. is preferable.

The heating time h is preferably at least one month, particularly at least 3 months. FIG. 4 shows a graph of such results, wherein a graph group (data group) shows the relationship between heating time h (axis of abscissa) and breaking elongation percentage E (axis of ordinate) at different heating temperatures w (w1–w4).

Then, the relationship between h and E at each value w is converted to a relationship between h and w at each value E. FIG. 5 shows one example, which is a graph group (data group) showing the relationship between heating temperature (axis of abscissa) and heating time (axis of ordinate) at different breaking elongation percentages E (100%, 150%, 200%, 250%, 300%); a so-called Arrhenius' curve. For explanation's sake, the limit of use Ez of breaking elongation percentage E is set to 100% and the graph is drawn with a thick line.

When the Arrhenius' curve of FIG. 5 is to be drawn based on the data read from FIG. 4, a linear equation (straight line) wherein the correlation coefficient becomes the smallest by the least square method, or quadratic equation or multidimensional equation is preferably determined. In most cases, the curve actually approaches a linear equation (straight line).

In step (3), the period of use (installation period) of an installed cable is considered to be the heating time h1 of the cable. When the breaking elongation percentage, as determined in step (1), of the covering layer of an actual cable is 250%, the heating temperature w1 corresponding to heating time h1 at point a is determined on the graph of E=250% in FIG. 5. On the graph of limit of use E=100%. (=EZ) in FIG. 5, the limit of heating time hz corresponding to heating temperature w1 at point b is determined. Lastly, the difference between the limit heating time hz and heating time (=installation period) h1 (hz–h1) is determined and taken as the remaining life.

The entire constitution of the deterioration diagnostic apparatus of the present invention is explained in the following.

Figure 3:
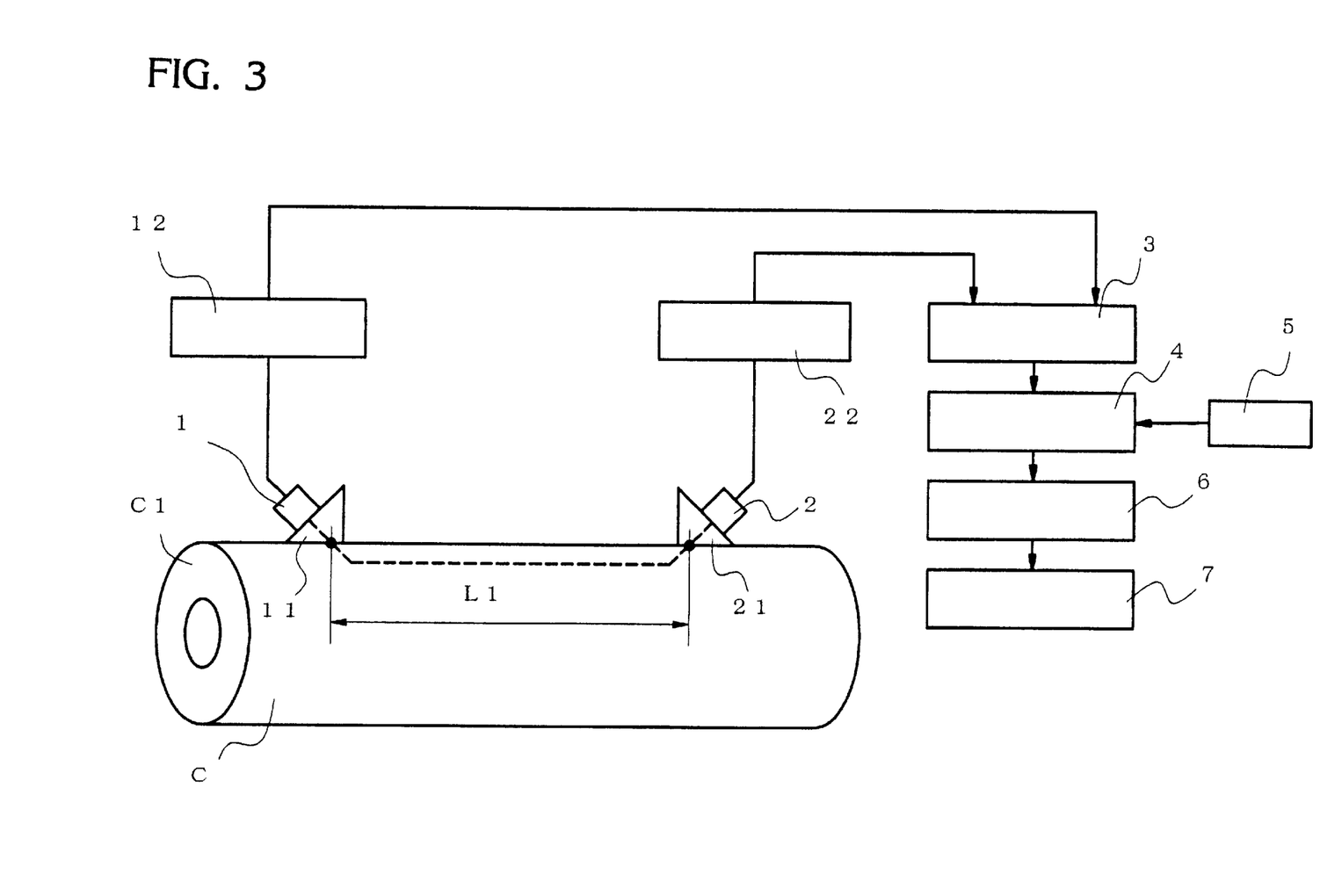
FIG. 3 shows the construction of the entire deterioration diagnostic apparatus of the present invention, wherein examples of the driving system, control system and operation system are shown in a block diagram.

FIG. 3 shows one example, wherein the positions of transmission control means 12, receipt control means 22, propagation time measuring means 3, operation means 4, distance input means 5, determination means 6 and display means 7 are shown, besides the constitution shown in FIG. 1.

The transmission control means 12 functions to enter the time of transmission of an ultrasonic wave from the transmitting means 1 and the like in the form of an electric signal into the propagation time measuring means 3 to be mentioned later. The receipt control means 22 functions to enter the time of receipt of an ultrasonic wave from the receiving means 2 and the like in the form of an electric signal into the propagation time measuring means 3. The propagation time measuring means 3 operates the time required from transmission to receipt based on the aforementioned signal. The method for measuring the propagation time is not limited to the above-mentioned method. For example, a counter or clock is set inside the propagation time measuring means 3, which is started and stopped to measure the propagation time according to a signal notifying the start of transmission from the transmission control means 12 and a signal notifying receipt from the receipt control means 22.

In the above-mentioned method (I), the intervals L1, L2 set between the transmitting means 1 and receiving means 2 are memorized by distance input means 5. The propagation times t1 and t2 are measured by the propagation time measuring means 3. The operation means 4 calculates the propagation velocity V from these data L1, L2, t1 and t2, as explained in the above.

The determination means 6 retains the data group for various deterioration diagnoses of the material of the covering layer. It converts the propagation characteristic value entered by the operation means 4 to a diagnostic characteristic value, judges the deterioration level, and sends the results to the display means 7 to allow display by various display methods, such as a relationship graph of operation days of insulating electric wire—deterioration degree, and the like.

The deterioration diagnostic apparatus of the present invention may be constructed by connecting individual devices. Every constituent except the measuring device (inclusive of ultrasonic wave piezoelectric transducer, detecting element, driving system of these drivers and the like) of the above-mentioned (A) may be integrally controlled by a computer. Depending on the constitution of an apparatus, a propagation time measuring means 3 may be externally mounted as an independent measurement device, which exchanges data with the computer.

The data group explained in the above is stored in the storage unit of a computer. The propagation characteristic may be operated at the stage of the measuring device of the above-mentioned (A), or in the central processing unit. In any case, the central processing unit takes out the diagnostic characteristic value corresponding to the obtained propagation characteristic from the data group for deterioration diagnosis, which is stored in the storage unit.

When the central processing unit in the deterioration diagnostic apparatus of the present invention is a computer, a deterioration diagnosis is preferably made using this computer. As a program for the diagnosis to be made, the above-mentioned (B) is exemplified. A typical deterioration diagnosis program is shown in the following. The propagation velocity is used as the propagation characteristic and the breaking elongation percentage is used as the diagnostic characteristic. In this program example, the kind and amount of the plasticizer, filler and the like to be added to the material of the covering layer explained earlier are taken into consideration in making a deterioration diagnosis.

Figure 6:
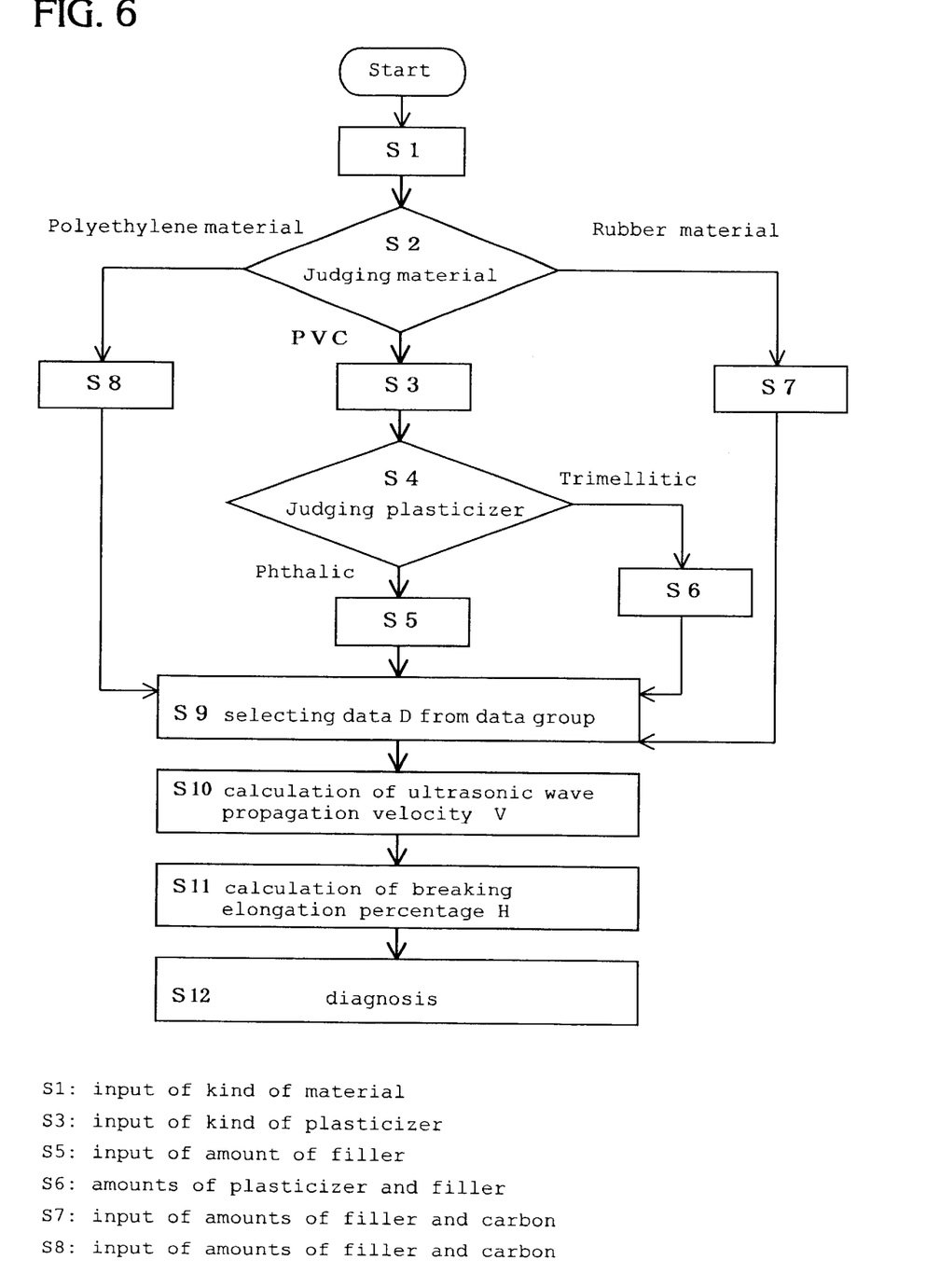
FIG. 6 is a flow chart showing the action included in the deterioration diagnosis program to be demonstrated by the deterioration diagnostic apparatus of the present invention.

As shown in the flow chart of FIG. 6, in step S1, the program first requires input of the kind of the organic polymer material which is the material of the covering layer. After input, it judges in step S2 if the kind of the material is polyvinyl chloride (PVC), of a rubber type or of a polyethylene type.

When the material is PVC in step S2, the program proceeds to step S3, where input of the kind of plasticizer is requested. After input, the program proceeds to step S4, where it judges if the plasticizer is of a phthalate ester type or trimellitate ester type.

In step S4, when the plasticizer is of a phthalate ester type, the program goes on to step S5, where it requests input of the amount of filler. After input, the program proceeds to step S9. When the plasticizer is of a trimellitate ester type in step S4, the program proceeds to step S6, where it requests input of the amounts of plasticizer and filler. After input, the program proceeds to step S9. When the plasticizer is not added, the program proceeds to step S5, where it requests input of the amount of filler. In case of no addition in steps S5 and S6, an operator inputs, for example, "zero", "0" and the like.

When the material is a rubber type material in step S2, the program moves on to step S7, where the amounts of filler and carbon are input, and then to step S9. As regards the substance not added, the operator inputs "zero" as in the above.

In step S2, when the material is a polyethylene type material, the program moves on to step S8, where the amounts of filler and carbon are input, and then to step S9. As regards the substance not added, the operator inputs "zero" as in the above.

When the information of the material of the covering layer is input as above, the program selects, as data D, the data having the same conditions as the information obtained from the data group in step S9. The data group is formed by the steps mentioned earlier and stored in various outside or inside storage units, recording media and the like.

In step S10, the propagation velocity V of the measured material of the covering layer is calculated from the values input from an outside measurement device. In step S11, the breaking elongation percentage H corresponding to the aforementioned propagation velocity V is determined from the data D. In step S12, the deterioration level of the material of the cable covering is diagnosed with this breaking elongation percentage H as an index of deterioration.

In FIG. 6, the kind of material, the kind and amount of plasticizer, the amount of filler and the amount of carbon have been input. However, this example is not limitative and at least one of these may be sufficient. For example, only the kind of material may be sufficient. It is also possible to make a program predict the remaining life.

EXAMPLES

Example 1

In this Example, the propagation characteristic of the covering layer of a cable was measured using the deterioration diagnostic apparatus of FIG. 1 and following the above-mentioned method (I).

The test target was a power cable immediately after production, which had a soft polyvinyl chloride sheath (covering layer) having an outer diameter of 21 mm and a nominal thickness of 2.5 mm. The transmitting means 1 and receiving means 2 were set on the surface of the covering layer of the cable respectively via a polyethylene tetrafluoride oblique delay chip (inclination:40°).

Two kinds of intervals L1, L2 were set to 1 mm and 10 mm and, using an ultrasonic wave having a frequency of 1.0 MHz, the propagation times t1 and t2 at L1 and L2, respectively, were measured, based on which the difference in propagation time (t2–t1) was determined. The number of data at t1 and t2 was each n=10. As a result, the average value of (t2–t1) was 4.86 $\mu$sec. From V=(L2–L1)/(t2–t1), the propagation velocity in the covering layer of 1850 m/sec was obtained.

A part of the covering layer of the above-mentioned cable was taken out and the propagation velocity thereof was accurately measured, which was 1852 m/sec. From this, the above-mentioned method (I) using the deterioration diagnostic apparatus of the present invention was confirmed to afford fine measurement of the propagation characteristic and is useful.

The above-mentioned cable was heated in an oven under air circulation at 130° C. for 10 days to cause deterioration. Using the above-mentioned method, t1 and t2 were measured and the propagation velocity in the covering layer was determined. As a result, the average value of (t2–t1) was 3.95 $\mu$sec, and the propagation velocity in the covering layer was 2280 m/sec. From this, it was confirmed that the propagation velocity changes with the growing deterioration of the material of the covering layer.

Example 2

In this Example, a data group, wherein the propagation characteristic and the diagnostic characteristic correspond to each other, was formed, the propagation characteristic of an actual article was measured, and the diagnostic characteristic corresponding to the measured value was obtained from the data group.

Instead of the measurement wherein the propagated distance is changed as in Example 1, a method, wherein the propagated distance is maintained constant and the diagnostic characteristic is obtained from the data group based on a single measurement of the propagation time, was applied.

The measurement target was a power cable installed for 10years and had a soft polyvinyl chloride covering layer, having an outer diameter of 21 mm and an actually measured thickness of 2.5 mm. In the same manner as in Example 1 except that the deterioration diagnostic apparatus of FIG. 1 was used and the interval (distance between the points of both delay chips) was set to 2 mm, the propagation time of the ultrasonic wave was measured.

A sheet (thickness 3 mm) made from the same material as the covering layer was used as a sample, and acceleratedly deteriorated by heating to give samples having various deterioration degrees. The correlation between the breaking elongation percentage and propagation time of the samples was separatedly established to form a data group. The propagation time of the sample was measured by the same method as used for the measurement of the above-mentioned power cable. From this data group, the breaking elongation percentage of about 220% was obtained, which corresponds to the propagation time measured with regard to the above-mentioned power cable.

A part of the covering layer of the above-mentioned power cable was taken out, punched out to give dumbbell sample pieces and the breaking elongation percentage of the samples was measured, which was 228% on average. From this, it was confirmed that the deterioration diagnostic method of the present invention provides the results that coincide well with those of the destructive inspection.

Example 3

In this Example, the remaining life was predicted as one of the deterioration diagnostic methods of the present invention. The target was a signal cable installed outdoor for 5 years, which was a 600V power cable consisting of a 1.0 mm diameter stranded copper conductor, a 1.0 mm thick polyvinyl chloride insulating layer formed thereon, and a 1.5 mm thick polyvinyl chloride covering layer (sheath) thereon. The polyvinyl chloride covering layer contained diisononylphthalate (50 parts by weight) as a plasticizer, tribasic lead sulfate (6 parts by weight) as a stabilizer and a brominated flame retardant (60parts by weight) as a filler, per 100 parts by weight of polyvinyl chloride. By the deterioration diagnostic method of the present invention, the breaking elongation percentage of the covering layer of the above-mentioned cable was known to be 272% (n=20) on average. The average sheath temperature during the 5 years of installation was about 40° C.

As a sample made from the same material as the above-mentioned covering layer, a 1.5 mm thick sheet was prepared. The sheet was heated in an oven under air circulation at 100–120° C.The changes in the breaking elongation percentage relative to the heating time were measured at each heating temperature w to obtain the results shown in FIG. 7.

Figure 7:
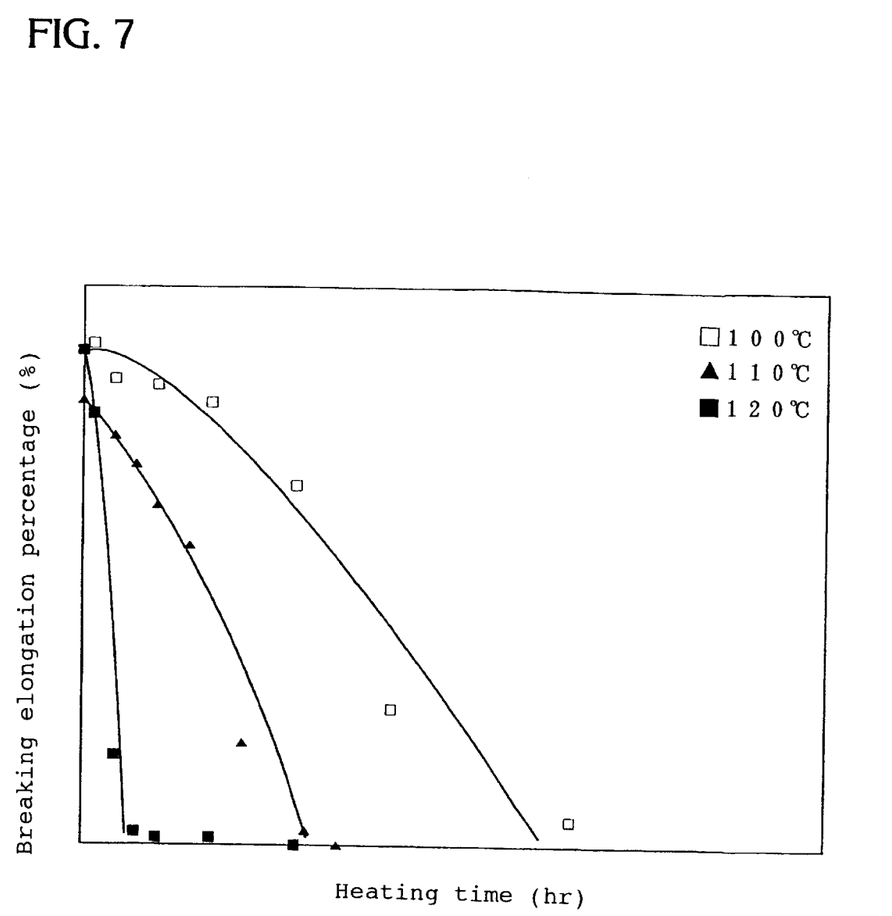
FIG. 7 is a graph showing the relationship between heating time and breaking elongation percentage at each heating temperature w obtained with regard the specimens in Examples of the present invention.
Figure 8:
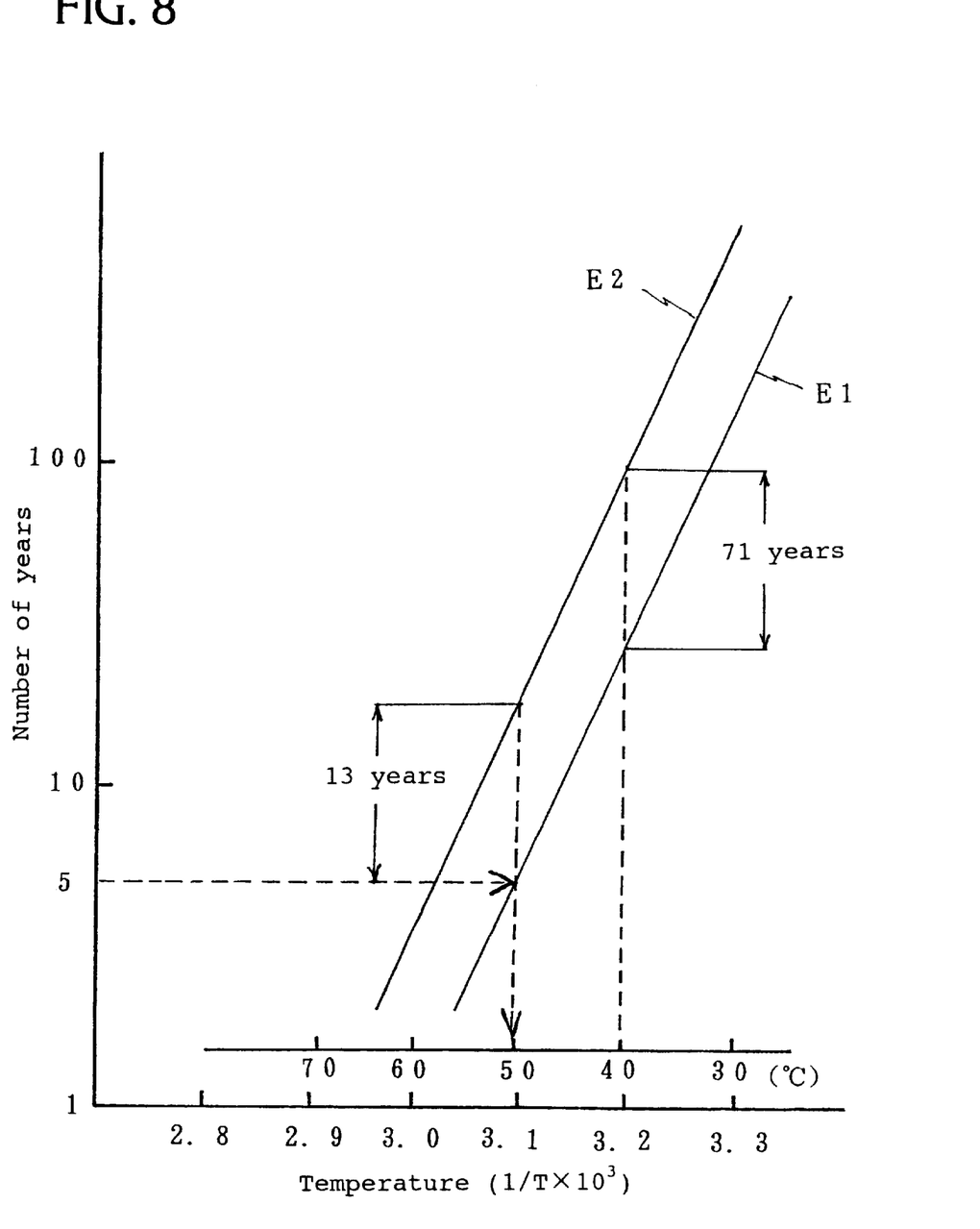
FIG. 8 is a graph showing the relationship between heating temperature and heating time at each breaking elongation percentage obtained with regard the specimens in Examples of the present invention.

Based on the data obtained from FIG. 7, an Arrhenius' plot was drawn to give the w–h correlation as a data group with the breaking elongation percentage as shown in FIG. 8 as a parameter. In FIG. 8, only the low temperature range necessary for the remaining life prediction is shown, wherein the axis of ordinate corresponding to the heating time in FIG. 7 is taken as "number of years" for the remaining life prediction. The curve E1 is an Arrhenius' curve wherein the breaking elongation percentage is 272% and the curve E2 is an Arrhenius' curve wherein the breaking elongation percentage is 230%.

From the curve E1 of FIG. 8, the temperature corresponding to the installation period of 5 years and the breaking elongation percentage of 272% is known to be about 50° C. When the breaking elongation percentage of 230% (curve E2) is taken as the limit of use, the time period necessary for the breaking elongation percentage to decrease to 230%, i.e., remaining life, is predicted to be about 13 years from FIG. 8.

The breaking elongation percentage of a different cable installed for 20 years under similar environment (average sheath temperature about 40° C.) was measured. As a result, deterioration was found to have proceeded to the breaking elongation percentage of 228% (n=20) on average. From this, the above-mentioned results of remaining life prediction was found to be industrially useful enough.

Comparative Example 3-1

The remaining life was predicted at 40° C. by a conventional method, supposing that the cable of the above-mentioned Example 3 is used at an average sheath temperature of 40° C. As a result, the predicted remaining life was 71 years from FIG. 8, which was vastly deviated from the above-mentioned confirmed results.

Example 4

In this Example, the remaining life was predicted with regard to the power cable installed outdoor for 9 years. The material of the covering layer (sheath) was an inflammable chloroprene. This cable was a 3300 V power cable having a 2.0 mm diameter stranded copper conductor, a 2.5 mm thick natural rubber insulating layer formed thereon, and a 1.8 mm thick covering layer thereon. The covering layer was made from chloroprene, which contained paraffin oil (20 parts by weight), aluminum silicate (60 parts by weight) as a filler, and carbon black (25 parts by weight) per 100 parts by weight of chloroprene and which was crosslinked by heating.

By the deterioration diagnostic method of the present invention, the breaking elongation percentage of the covering layer of the above-mentioned power cable was known to be 378% (n=20) on average. The average sheath temperature during the 9 years of installation was about 45° C.

As a sample made from the same material as the above-mentioned covering layer, a 2 mm thick sheet was prepared by press forming crosslinking at 150° C. for 30 minutes. This sheet was heated in an oven under air circulation at 120–150° C. and the changes in the breaking elongation percentage relative to the heating time were measured at each heating temperature w. In the same manner as in Example 3, an Arrhenius' plot was drawn to give a linear w–h correlation as a data group with a breaking elongation percentage as a parameter. From the thus obtained data group (w–h correlation), the temperature corresponding to the 9 years of installation and the breaking elongation percentage of 378% was about 58° C.

The breaking elongation percentage of 300% was set as the limit of use, and from the w–h correlation at the breaking elongation percentage of 300%, the period before reaching the limit of use was predicted to be about 7.5 years.

The breaking elongation percentage of a different cable installed for 19 years under similar environment (average sheath temperature about 45° C.) was measured. As a result, deterioration was found to have proceeded to the breaking elongation percentage of 298% (n=20) on average. From this, the above-mentioned results of remaining life prediction was found to be industrially useful enough.

Comparative Example 4-1

The remaining life was predicted at 45° C. by a conventional method, supposing that the cable of the above-mentioned Example 4 is used at an average sheath temperature of 45° C. As a result, the predicted remaining life was 39 years, which was vastly deviated from the above-mentioned confirmed results.

Example 5

In this Example, deterioration of the covering layer of a cable was diagnosed in consideration of the kind and amount of plasticizer and filler to be added to the material of the covering layer.

[Information of Material of Covering Layer and Selection of Data D]

The information of the material of the covering layer of an installed cable was obtained from the records, as mentioned earlier. As a result, the kind of the polymer material was polyvinyl chloride, the plasticizer was a phthalate ester type plasticizer, and the amount of the filler was 60 parts by weight. Based on this information, data D was selected from the data group prepared in advance.

[Deterioration Diagnosis of Covering Layer of Cable]

With regard to the material of the covering layer of the above-mentioned diagnosis target cable, the time from the transmission of an ultrasonic wave to the receipt thereof was measured using a commercially available ultrasonic wave probe, and the ultrasonic wave propagation velocity in the covering material was calculated and found to be 2150 m/s. The breaking elongation percentage corresponding to the measured value was obtained from the selected data D, which was 190%.

[Evaluation]

The covering layer of the above-mentioned diagnosis target cable was determined for the breaking elongation percentage by a conventional method ignoring the kind and amount of the plasticizer, filler and the like. As a result, the breaking elongation percentage was 140%.

The covering layer of the cable which was the target of the above-mentioned diagnosis was destroyed. A test piece was taken out and subjected to the actual measurement of the breaking elongation percentage thereof by a tensile test to obtain a value of 190%.

From the above, the deterioration diagnostic method of the present invention that takes the kind and amount of the plasticizer, filler and the like into consideration was found to provide a result nearer to the destructive inspection results and to be a useful method.

The deterioration diagnostic method of this Example was formed into a computer program as shown in the flow chart of FIG. 6, and run in a computer, which provided a quicker diagnosis.

Industrial Applicability

The present invention is suitable for the diagnosis of the deterioration degree of the covering layer of an article requiring a non-destructive diagnosis, such as a power cable in operation. According to the deterioration diagnostic method of the present invention, the propagation characteristic of a covering layer can be measured non-destructively and more accurately without the data of the thickness and the like of the covering layer. Therefore, the diagnostic characteristic obtained from the data group becomes more accurate. In addition, the introduction of "time elapsed" into the data group has enabled an overall deterioration diagnosis inclusive of changes with the time elapsed, thus making possible a more accurate prediction of remaining life than by a conventional method.

This application is based on application Nos. 320863/1997, 143852/1998, 154915/1998, 154929/1998 and 160344/1998 filed in Japan, the contents of which are incorporated hereinto by reference.

What is claimed is:

1. A deterioration diagnostic method for diagnosis of deterioration of an article having at least a covering layer made from an organic polymer material, which comprises the steps of:
(i) forming a data group for deterioration diagnosis comprising deterioration diagnostic characteristic values and corresponding ultrasonic wave propagation characteristic values for samples having different material specifications, wherein the data group is prepared by:
 (a) providing the samples having different material specifications wherein the material specifications consist of one or more factors selected from the group consisting of a kind of organic polymer material, a kind of plasticizer, an amount of plasticizer, an amount of filler, and an amount of carbon, added to the organic polymer material, and
 (b) measuring deterioration diagnostic characteristics and corresponding ultrasonic wave propagation characteristics for the samples
(ii) propagating an ultrasonic wave through a surface and near the surface of the covering layer of the article to measure an ultrasonic wave propagation characteristic of the covering layer, and
(iii) determining a corresponding deterioration diagnostic characteristic from the data group for the ultrasonic wave propagation characteristic of the covering layer.

2. The deterioration diagnostic method of claim 1, wherein the article is a cable.

3. The deterioration diagnostic method of claim 1, wherein the deterioration diagnostic characteristic is a breaking elongation percentage.

4. The deterioration diagnostic method of claim 1, wherein the data group for deterioration diagnosis comprises a deterioration diagnostic characteristic value that varies with elapsed time, and an ultrasonic wave propagation characteristic value that varies corresponding to the deterioration diagnostic characteristic value.

5. The deterioration diagnostic method of claim 1, wherein the ultrasonic wave propagation characteristic is a propagation velocity of an ultrasonic wave, which velocity is measured by a method comprising the steps of setting an ultrasonic wave transmitting means and an ultrasonic wave receiving means on the surface of a measurement target respectively via a delay chip, thereby to make an ultrasonic wave sent from the transmitting means linearly propagated in the measurement target to the position of the receiving means and received by the receiving means, measuring propagation times t1 and t2 of the ultrasonic wave when the intervals between the transmitting means and the receiving means are L1 and L2, respectively, and calculating (L2−L1)(t2−t1) to give the propagation velocity of the ultrasonic wave.

6. The deterioration diagnostic method of claim 1, wherein the ultrasonic wave propagation characteristic is a propagation time of an ultrasonic wave that has been propagated a certain distance, which propagation time is measured by the steps of setting an ultrasonic wave transmitting means and an ultrasonic wave receiving means via a delay chip at the certain distance on the surface of a test target which is a covering layer of a specimen or article, and measuring a time necessary for the ultrasonic wave sent from the transmitting means to be linearly propagated through the test target to the position of the receiving means and received by the receiving means via the delay chip.

7. The deterioration diagnostic method of claim 1, wherein the article is an installed cable, and the deterioration diagnosis is made with regard to a part showing a greater degree of a deteriorating factor, after measuring the distribution of deteriorating factors that deteriorate a covering layer of the cable along the longitudinal direction of the cable.

8. The deterioration diagnostic method of claim 7, wherein the distribution of the deteriorating factors is measured by setting measuring means capable of measuring the degree of deteriorating factors in at least one part of the installed cable along the longitudinal direction thereof.

9. The deterioration diagnostic method of claim 1, wherein the method determines a remaining life by the steps of taking the deterioration diagnostic characteristic value of the covering layer of the article as E1, measuring a heating temperature t and a corresponding heating time h at various deterioration diagnostic characteristic values after changing the deterioration diagnostic characteristic value, inclusive of limit of use value Ez, for a specimen made of the same material as the covering layer, to give a data group used for remaining life prediction, determining a heating temperature t1 corresponding to the heating time h1 at the deterioration diagnostic characteristic value of E1, using the data group for remaining life prediction and regarding the period of use of the article as a heating time h1, determining a heating time hz corresponding to the heating temperature t1 at the limit of use value Ez of the deterioration diagnostic characteristic, and giving a value of hz−h1 as the remaining life.

10. A deterioration diagnostic apparatus for diagnosing deterioration of an article having at least a covering layer made from an organic polymer material, which comprises:

(i) a device for measuring ultrasonic wave propagation characteristics, wherein a covering layer of an article or a specimen of a covering layer is a measurement target, said device comprising:

(a) an ultrasonic wave transmitting means, (b) an ultrasonic wave receiving means, (c) a delay chip to be intervened when said transmitting means and said reciving means means are set on the surface of the measurement target, wherein the delay chip has an inclination and material that have been determined such that the propagating direction of the ultrasonic wave changes when enters the measurement target from the delay chip, as a result of which the ultrasonic wave is propagated through the surface and near surface of the measurement target, and (d) a propagation time measuring means to measure the time spent from transmission of an ultrasonic wave from the transmitting means to receipt of the ultrasonic wave by the receiving means, (ii) a storage unit of a computer containing a data group for deterioration diagnosis, which consists of a deterioration diagnostic characteristic value that varies with elapsed time and a corresponding ultrasonic wave propagation characteristic value of the material of the covering layer of an article that varies in response to the deterioration diagnostic characteristic value, and (iii) a central processing unit of a computer that takes out, from the data group, a deterioration diagnostic characteristic value corresponding to the ultrasonic wave propagation characteristic value of the covering layer of the article as obtained using the measuring device, and executes a deterioration diagnosis program comprising at least the steps of:

(a) inputting material specification information for a covering layer of a diagnosis target article, (b) selecting a data group for deterioration diagnosis having the same input material specification as the covering layer of the article, (c) inputting an ultrasonic wave propagation characteristic value obtained for the covering layer of the article, and (d) determining a deterioration diagnostic characteristic value from the data group corresponding to the ultrasonic wave propagation characteristic value of the covering layer of the article.

11. The deterioration diagnostic apparatus of claim 10, wherein the delay chip is made from a material that has a propagation velocity of an ultrasonic wave that is less than a propagation velocity of the ultrasonic wave in the organic polymer material.

12. The deterioration diagnostic apparatus of claim 10, wherein the article is a cable.

13. The deterioration diagnostic apparatus of claim 10, wherein the deterioration diagnostic characteristic is a breaking elongation percentage.

14. The deterioration diagnostic apparatus of claim 10, further comprising a means for measuring an interval set between the ultrasonic wave transmitting means and the ultrasonic wave receiving means on the covering layer.

15. The deterioration diagnostic apparatus of claim 10, wherein the data group for deterioration diagnosis comprises deterioration diagnostic characteristic values and corresponding ultrasonic wave propagation characteristic values of samples having different material specification, which values being obtained by changing the material specification consisting of one or more factors selected from the group consisting of a kind of an organic polymer material, a kind and an amount of a plasticizer, an amount of a filler and an amount of carbon, added to the organic polymer material.

* * * * *